United States Patent [19]

Clark et al.

[11] Patent Number: 5,965,754
[45] Date of Patent: Oct. 12, 1999

[54] PROCESS FOR THE DIRECT OXIDATION OF OLEFINS TO OLEFIN OXIDES

[75] Inventors: Howard W. Clark; Robert G. Bowman; Joseph J. Maj, all of Midland, Mich.; Simon R. Bare, Glen Ellyn, Ill.; George E. Hartwell, Midland, Mich.

[73] Assignee: The Dow Chemical Company, Midland, Mich.

[21] Appl. No.: 09/209,699

[22] Filed: Dec. 11, 1998

Related U.S. Application Data

[63] Continuation of application No. PCT/US97/11417, Jun. 30, 1997, which is a continuation-in-part of application No. 08/679,605, Jul. 11, 1996, abandoned
[60] Provisional application No. 60/021,013, Jul. 1, 1996, provisional application No. 60/026,590, Sep. 20, 1996, and provisional application No. 60/026,591, Sep. 20, 1996.

[51] Int. Cl.$^6$ .................... C07D 301/10; B01J 21/08; B01J 23/66
[52] U.S. Cl. .................... 549/533; 549/523; 502/243; 502/344
[58] Field of Search .................... 549/523, 533; 502/243, 344

[56] References Cited

U.S. PATENT DOCUMENTS

| | | | |
|---|---|---|---|
| 4,391,756 | 7/1983 | Kuch et al. | 260/430 |
| 4,839,327 | 6/1989 | Haruta et al. | 502/243 |
| 5,008,414 | 4/1991 | Ramachandran et al. | 549/538 |

FOREIGN PATENT DOCUMENTS

| | | |
|---|---|---|
| 0 200 260 A2 | 12/1986 | European Pat. Off. . |
| 0 638 362 A1 | 2/1995 | European Pat. Off. . |
| 0 709 360 A1 | 5/1996 | European Pat. Off. . |
| 0 723 810 A1 | 7/1996 | European Pat. Off. . |
| 0 850 936 A1 | 7/1998 | European Pat. Off. . |
| 196 00 709 A1 | 7/1997 | Germany . |
| 4-352771 | 12/1992 | Japan . |
| 7-8797 | 1/1995 | Japan . |
| 7-53577 | 6/1995 | Japan . |
| 8-269029 | 10/1996 | Japan . |
| 10-5590 | 1/1998 | Japan . |
| 1 409 421 | 10/1975 | United Kingdom . |
| 96/02323 A1 | 2/1996 | WIPO . |
| 97/25143 A1 | 7/1997 | WIPO . |
| 97/34692 A1 | 9/1997 | WIPO . |
| 97/47386 | 12/1997 | WIPO . |

OTHER PUBLICATIONS

Haruta, Masatake, "Catalysis of Ultra–fine Gold Particles Deposited on Metal Oxides", Workshop on Environmental Catalysis: The Role of 1B Metals, Ikeda, Osaka, Japan (Nov. 2–3, 1995) pp. 109–118.

Hayashi, Toshio et al., "Selective Partical Oxidation of Hydrocarbons over Au/TiO$_2$ Catalysts", Symposium on Heterogeneous Hydrocarbon Oxidation Presented before the Division of Petroleum Chemistry, Inc., 211$^{th}$ National Meeting, American Chemical Society, New Orleans, LA (Mar. 24–29, 1996) pp. 71–74.

Kalvachev, Yuri A. et al., "Selective Partial Oxidation of Propylene to Propylene Oxide on Au/Ti–MCM Catalysts in the Presence of Hydrogen and Oxygen", 3$^{rd}$ World Congress on Oxidation Catalysis, R. K. Grasselli et al. (Editors), Elsevier Science B.V. (Pub.) (Sep. 24, 1997) pp. 965–972.

*Primary Examiner*—Ba K. Trinh
*Attorney, Agent, or Firm*—Marie F. Zuckerman; John B. Treangen

[57] ABSTRACT

A process and catalyst for the direct oxidation of an olefin having three or more carbon atoms, such as propylene, by oxygen to an olefin oxide, such as propylene oxide. The process involves contacting the olefin with oxygen under reaction conditions in the presence of hydrogen and a catalyst. The catalyst comprises gold on a support of titanium dispersed on silica. The titanium phase is disorganized and substantially free of crystalline titanium dioxide, as determined by analytical methods, such as, high resolution transmission electron microscopy and Raman spectroscopy. Selectivity to olefin oxide is high at good conversions of the olefin. The time between catalyst regenerations is long, and the catalyst is readily regenerated.

74 Claims, No Drawings

PROCESS FOR THE DIRECT OXIDATION OF OLEFINS TO OLEFIN OXIDES

CROSS-REFERENCES TO RELATED APPLICATIONS

This application is a continuation of International Patent Application No. PCT/US97/11417, filed Jun. 30, 1997, which was a continuation-in-part of U.S. application Ser. No. 08/679,605, filed Jul. 11, 1996, now abandoned. This application also claims the benefit of U.S. Provisional Application No. 60/021013, filed Jul. 1, 1996, U.S. Provisional Application No. 60/026590, filed Sep. 20, 1996, and U.S. Provisional Application No. 60/026591, filed Sep. 20, 1996.

This invention was made with United States Government support under Award Number 70NANB5H1143 awarded by The National Institute of Standards and Technology. The United States Government has certain rights in the invention.

BACKGROUND OF THE INVENTION

This invention pertains to a process and catalyst for the direct oxidation of olefins, such as propylene, by oxygen to olefin oxides, such as propylene oxide.

Olefin oxides, such as propylene oxide, are used to alkoxylate alcohols to form polyether polyols, such as polypropylene polyether polyols, which find significant utility in the manufacture of polyurethanes and synthetic elastomers. Olefin oxides are also important intermediates in the manufacture of alkylene glycols, such as propylene glycol and dipropylene glycol, and alkanolamines, such as isopropanolamine, which are useful as solvents and surfactants.

Propylene oxide is produced commercially via the well-known chlorohydrin process wherein propylene is reacted with an aqueous solution of chlorine to produce a mixture of propylene chlorohydrins. The chlorohydrins are dehydrochlorinated with an excess of alkali to produce propylene oxide. This process suffers from the production of a low concentration salt stream. (See K. Weissermel and H. J. Arpe, *Industrial Organic Chemistry*, $2^{nd}$ ed., VCH Publishers, Inc., New York, N.Y., 1993, p. 264–265.)

Another well-known route to olefin oxides relies on the transfer of an oxygen atom from an organic hydroperoxide or peroxycarboxylic acid to an olefin. In the first step of this oxidation route, a peroxide generator, such as isobutane or acetaldehyde, is autoxidized with oxygen to form a peroxy compound, such as t-butyl hydroperoxide or peracetic acid. This compound is used to epoxidize the olefin, typically in the presence of a transition metal catalyst, including titanium, vanadium, molybdenum, and other heavy metal compounds or complexes. Along with the olefin oxide produced, this process disadvantageously produces equimolar amounts of a coproduct, for example an alcohol, such as t-butanol, or an acid, such as acetic acid, whose value must be captured in the market place. (*Industrial Organic Chemistry*, ibid., p. 265–269.)

Although the direct oxidation of ethylene by molecular oxygen to ethylene oxide has been commercialized with a silver catalyst, it is known that the analogous direct oxidation of propylene exhibits a low selectivity to the olefin oxide. Disadvantageously large amounts of acrolein and oxygen-containing $C_{1-3}$ byproducts are produced. (See *Industrial Organic Chemistry*, ibid., p. 264.) Some patents represented by U.S. Pat. No. 4,007,135 and U.S. Pat. No. 4,845,253, teach the use of metal-promoted silver catalysts for the oxidation of propylene with oxygen to propylene oxide. Among the metal promoters disclosed are gold, beryllium, magnesium, calcium, barium, strontium, and the rare earth lanthanides. These promoted silver catalysts also exhibit low selectivities to the olefin oxide.

Alternatively, EP-A 1-0,709,360 discloses a process of oxidizing an unsaturated hydrocarbon, such as propylene, with oxygen in the presence of hydrogen and a catalyst to form an epoxide, such as propylene oxide. Gold deposited on titanium dioxide, preferably the anatase phase of crystalline titanium dioxide, further immobilized on a carrier such as silica or alumina, is taught as the catalyst composition. The catalyst exhibits lower olefin oxide selectivity and less efficient hydrogen consumption when operated at higher temperatures. Additionally, the catalyst has a short run time.

PCT publication WO-A1-96/02323 discloses the oxidation of an olefin, including propylene, with oxygen in the presence of hydrogen and a catalyst to form an olefin oxide. The catalyst is a titanium or vanadium silicalite containing at least one platinum group metal, and optionally, an additional metal selected from gold, iron, cobalt, nickel, rhenium, and silver. The productivity of olefin oxide is low in this process.

In view of the above, a need exists in the chemical industry for an efficient direct route to propylene oxide and higher olefin oxides from the reaction of oxygen with $C_3$ or higher olefins. The discovery of such a process which simultaneously achieves high selectivity to the olefin oxide at an economically advantageous conversion of the olefin would represent a significant achievement over the prior art. For commercial viability such a process would also require that the catalyst exhibit a long lifetime.

In another aspect, U.S. Pat. No. 4,937,219 discloses a composition comprising gold particles having a particle size smaller than about 500 Å immobilized on an alkaline earth oxide or titanium oxide. It is disclosed that the preparation of this composition involves deposition of a gold compound onto the alkaline earth or titanium oxide followed by calcination so as to form metallic gold having a particle size smaller than about 500 Å. This teaching is silent with respect to a process of preparing olefin oxides.

SUMMARY OF THE INVENTION

This invention is a novel process of preparing an olefin oxide directly from an olefin and oxygen. The process comprises contacting an olefin having at least three carbon atoms with oxygen in the presence of hydrogen and in the presence of a catalyst under process conditions sufficient to produce the corresponding olefin oxide. The unique catalyst which is employed in the process of this invention comprises gold on a support, wherein the support comprises titanium dispersed on silica. The titanium is substantially present in a disorganized phase. As used herein, the term "disorganized phase" means that the titanium is scattered over the silica such that essentially no crystalline titanium dioxide is detectable, as measured by the analytical techniques described hereinafter. For the purposes of this invention, crystalline phases are regarded as "organized" based on their structural regularity and periodicity.

The novel process of this invention is useful for producing an olefin oxide directly from oxygen and an olefin having three or more carbon atoms. Unexpectedly, the process of this invention produces the olefin oxide in a remarkably high selectivity. Partial and complete combustion products, such as acrolein and carbon dioxide, which are found in large amounts in many prior art processes, are produced in lesser amounts in the process of this invention. Significantly, the process of this invention can be operated at a high temperature, specifically greater than about 120° C., while maintaining high selectivity to the olefin oxide. Operation at higher temperatures advantageously provides steam credits from the heat produced. Accordingly, the process of this invention can be integrated into a total plant design wherein the heat derived from the steam is used to drive additional processes, for example, the separation of the olefin oxide from water. Since water is produced as a coproduct of this process, even more advantageously, the hydrogen efficiency in the process of this invention, as measured by the water to olefin oxide molar ratio, is good. Most advantageously, the process in its preferred embodiments exhibits an olefin conversion which is good.

In another aspect, this invention is a unique catalyst composition comprising gold on a support, wherein the support comprises titanium dispersed on silica. As noted hereinabove, the titanium is present substantially in a disorganized phase.

The novel composition of this invention can be effectively used in the aforementioned direct oxidation of an olefin having three or more carbon atoms to the corresponding olefin oxide. Besides being active and highly selective for the olefin oxide, the catalyst exhibits evidence of a long lifetime. When finally exhausted, the catalyst is easy to regenerate. Accordingly, this unique catalyst possesses highly desirable properties for the process of oxidizing propylene and higher olefins to their corresponding olefin oxides.

DETAILED DESCRIPTION OF THE INVENTION

The novel process of this invention comprises contacting an olefin having three or more carbon atoms with oxygen in the presence of hydrogen and an epoxidation catalyst under process conditions sufficient to prepare the corresponding olefin oxide. In one preferred embodiment, a diluent is employed with one or more of the reactants, as described in detail hereinafter. The relative molar quantities of olefin, oxygen, hydrogen, and optional diluent can be any which are sufficient to prepare the desired olefin oxide. In a preferred embodiment of this invention, the olefin is a $C_{3-12}$ olefin, and it is converted to the corresponding $C_{3-12}$ olefin oxide. In a more preferred embodiment, the olefin employed is a $C_{3-8}$ olefin, and it is converted to the corresponding $C_{3-8}$ olefin oxide. In a most preferred embodiment, the olefin is propylene, and the olefin oxide is propylene oxide.

The novel catalyst which is employed in the epoxidation process of this invention comprises gold on a support wherein the support comprises titanium dispersed on silica. The titanium is present preferably in a valence state higher than zero. In addition, the titanium is substantially present in a disorganized phase. As used herein, the phrase "substantially present in a disorganized phase" means that greater than about 80 weight percent of the titanium is present in the disorganized phase. In this phase, the titanium ions are scattered over the silica in such a manner that essentially no crystalline phases of titanium dioxide are detectable. The distinction between organized and disorganized phases can be made using high resolution transmission electron microscopy (HR-TEM) and/or Raman spectroscopy, as described in detail hereinafter.

Any olefin containing three or more carbon atoms can be employed in the process of this invention. Monoolefins are preferred, but compounds containing two or more olefins, such as dienes, can also be used. The olefin can be a simple hydrocarbon containing only carbon and hydrogen atoms; or alternatively, the olefin can be substituted at any of the carbon atoms with an inert substituent. The term "inert", as used herein, requires the substituent to be substantially non-reactive in the process of this invention. Suitable inert substituents include, but are not limited to, halides, ether, ester, alcohol, and aromatic moieties, preferably, chloro, $C_{-1}$-2 ether, ester, and alcohol moieties, and $C_{6-12}$ aromatic moieties. Non-limiting examples of olefins which are suitable for the process of this invention include propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including preferably 1-octene, and other higher analogues of these; as well as butadiene, cyclopentadiene, dicyclopentadiene, styrene, a-methylstyrene, divinylbenzene, allyl chloride, allyl alcohol, allyl ether, allyl ethyl ether, allyl butyrate, allyl acetate, allyl benzene, allyl phenyl ether, allyl propyl ether, and allyl anisole. Preferably, the olefin is an unsubstituted or substituted $C_{3-12}$ olefin, more preferably, an unsubstituted or substituted $C_{3-8}$ olefin. Most preferably, the olefin is propylene. Many of the aforementioned olefins are available commercially; others can be prepared by chemical processes known to those skilled in the art.

The quantity of olefin can vary over a wide range provided that the corresponding olefin oxide is produced in the process. Generally, the quantity of olefin employed depends upon the specific process features, including for example, the design of the reactor, the specific olefin, and economic and safety considerations. Those skilled in the art will know how to determine a suitable range of olefin concentrations for the specific process features. Typically, on a molar basis an excess of olefin is used relative to the oxygen, because this condition enhances the productivity to olefin oxide. In light of the disclosure herein, the quantity of olefin is typically greater than about 1, preferably, greater than about 10, and more preferably, greater than about 20 mole percent, based on the total moles of olefin, oxygen, hydrogen, and optional diluent. Typically, the quantity of olefin is less than about 99, preferably, less than about 85, and more preferably, less than about 70 mole percent, based on the total moles of olefin, oxygen, hydrogen, and optional diluent.

Oxygen is also required for the process of this invention. Any source of oxygen is acceptable, including air or essentially pure molecular oxygen. Other sources of oxygen may be suitable, including ozone and nitrogen oxides, such as nitrous oxide. Molecular oxygen is preferred. The quantity of oxygen employed can vary over a wide range provided that the quantity is sufficient for producing the desired olefin oxide. Ordinarily, the number of moles of oxygen per mole of olefin used in the feedstream is less than 1. Under these conditions the conversion of olefin and selectivity to olefin oxide are enhanced while the selectivity to combustion products, such as carbon dioxide, is minimized. Preferably, the quantity of oxygen is greater than about 0.01, more preferably, greater than about 1, and most preferably greater than about 5 mole percent, based on the total moles of olefin, hydrogen, oxygen, and optional diluent. Preferably, the quantity of oxygen is less than about 30, more preferably, less than about 25, and most preferably less than about 20 mole percent, based on the total moles of olefin, hydrogen, oxygen, and optional diluent. Above about 20 mole percent, the concentration of oxygen may fall within the flammable range for olefin-hydrogen-oxygen mixtures.

Hydrogen is also required for the process of this invention. In the absence of hydrogen, the activity of the catalyst is significantly decreased. Any source of hydrogen can be used in the process of this invention, including for example, molecular hydrogen obtained from the dehydrogenation of hydrocarbons and alcohols. In an alternative embodiment of this invention, the hydrogen may be generated in situ in the olefin oxidation reactor, for example, by dehydrogenating alkanes, such as propane or isobutane, or alcohols, such as isobutanol. Alternatively, hydrogen may be used to generate a catalyst-hydride complex or a catalyst-hydrogen complex which can provide the necessary hydrogen to the process.

Any quantity of hydrogen can be employed in the process provided that the amount is sufficient to produce the olefin oxide. Suitable quantities of hydrogen are typically greater than about 0.01, preferably, greater than about 0.1, and more preferably, greater than about 3 mole percent, based on the total moles of olefin, hydrogen, oxygen, and optional diluent. Suitable quantities of hydrogen are typically less than about 50, preferably, less than about 30, and more preferably, less than about 20 mole percent, based on the total moles of olefin, hydrogen, oxygen, and optional diluent.

In addition to the above reagents, it may be desirable to employ a diluent with the reactants, although the use thereof is optional. Since the process of this invention is exothermic, a diluent beneficially provides a means of removing and dissipating the heat produced. In addition the diluent provides an expanded concentration regime in which the reactants are non-flammable. The diluent can be any gas or liquid which does not inhibit the process of this invention. The specific diluent chosen will depend upon the manner in which the process is conducted. For example, if the process is conducted in a gas phase, then suitable gaseous diluents include, but are not limited to, helium, nitrogen, argon, methane, carbon dioxide, steam, and mixtures thereof. Most of these gases are essentially inert with respect to the process of this invention. Carbon dioxide and steam may not necessarily be inert, but may exhibit a beneficial promoting effect. If the process is conducted in a liquid phase, then the diluent can be any oxidation stable and thermally stable liquid. Examples of suitable liquid diluents include aliphatic alcohols, preferably $C_{1-10}$ aliphatic alcohols, such as methanol and t-butanol; chlorinated aliphatic alcohols, referably $C_{1-10}$ chlorinated alkanols, such as chloropropanol; chlorinated aromatics, preferably chlorinated benzenes, such as chlorobenzene and dichlorobenzene; as well as liquid polyethers, polyesters, and polyalcohols.

If a diluent is used, the amount of diluent is typically greater than about 0, preferably greater than about 0.1, and more preferably, greater than about 15 mole percent, based on the total moles of olefin, oxygen, hydrogen, and optional diluent. The amount of diluent is typically less than about 90, preferably, less than about 80, and more preferably, less than about 70 mole percent, based on the total moles of olefin, oxygen, hydrogen, and diluent.

The concentrations of olefin, oxygen, hydrogen, and diluent disclosed hereinabove are suitably based on the reactor designs and process parameters disclosed herein. Those skilled in the art will recognize that concentrations other than those disclosed herein may be suitably employed in other various engineering realizations of the process.

The unique catalyst which is beneficially employed in the process of this invention comprises gold on a support. The gold predominantly exists as elemental metallic gold, as determined by X-ray absorption spectroscopy or X-ray photoelectron spectroscopy, although gold in higher oxidation states may also be present. Most of the gold appears from TEM studied to be on the surface of the support. The deposition of individual gold atoms or small gold clusters on the support may also occur. Typically, the average size (or diameter) of the gold particles is about 10 Å or greater, as measured by TEM. Preferably, the average gold particle size is greater than about 10 Å, more preferably, greater than about 12 Å, and most preferably, greater than about 25 Å. Preferably, the average gold particle size is less than about 500 Å, more preferably, less than about 200 Å, and most preferably, less than about 100 Å.

The support used in the catalyst of this invention comprises titanium dispersed on silica. Commercial supports meeting the criteria described herein are suitably employed, or alternatively, the support can be prepared by the methods described hereinbelow. Preferably, the titanium exists predominantly in a positive oxidation state, as determined by X-ray photoelectron and X-ray absorption spectroscopies. More preferably, the titanium exists predominantly in an oxidation state of about +2 or higher, most preferably, in an oxidation state of from about +3 to about +4. The titanium is dispersed over the surface of the silica substantially in a disorganized phase. The term "substantially" means that greater than about 80 weight percent of the titanium exists in the disorganized phase. Preferably, greater than about 85, even more preferably, greater than about 90, and most preferably, greater than about 95 weight percent of the titanium exists in the disorganized phase. This result implies that typically less than about 20, preferably, less than about 15, even more preferably, less than about 10, and most preferably, less than about 5 weight percent of the titanium in the support exists in an organized crystalline form, specifically crystalline titanium dioxide. Thus, in its typical form, the support is substantially free of crystalline titanium dioxide, and in its most preferred form, essentially free of crystalline titanium dioxide. In another preferred embodiment, the gold particles are preferentially associated with the disorganized titanium phase rather than with any crystalline phase of titanium dioxide which may be present. TEM and Energy Dispersive X-ray analysis (EDX) can be used to image the association of gold particles with titanium.

The titanium ions in the disorganized phase may be isolated from other titanium ions, or alternatively, the titanium ions may be linked through oxide bonds to other titanium ions in small domains of a two-dimensional monolayer network. Whatever its actual topology, the disorganized phase does not exhibit an organized, periodic crystallinity. In another aspect of this invention, the titanium ions preferably occupy sites of substantially four or five-fold coordination or distorted variations thereof, as opposed to octahedral coordination. In its broadest concept, however, the disorganized phase of titanium is not limited to any particular topology or coordination.

The disorganized titanium phase can be distinguished from bulk crystalline titanium dioxide by high resolution transmission electron microscopy (HR-TEM) and/or by Raman spectroscopy, as described hereinbelow. Additionally, the disorganized phase does not exhibit a distinct X-ray diffraction (XRD) pattern. X-ray diffraction (XRD), however, is less sensitive in detecting crystalline titanium dioxide. Accordingly, the absence of an XRD pattern characteristic of the bulk crystalline phases of titanium dioxide is not conclusive evidence that these phases are absent in the support. Ultraviolet-Visible Diffuse Reflectance Spectroscopy (UV-VIS DRS) also can be used to confirm differences between the disorganized titanium phase and crystalline titanium dioxide. Typically, any one of HR-TEM, Raman, or UV-VIS DRS are used to identify the disorganized phase. Preferably, two or more of these methods are used to identify the disorganized phase. As a fourth method, titanium K-edge X-Ray Absorption Near Edge Structure (XANES) spectroscopy can be used in a complementary manner with HR-TEM, Raman and/or UV-VIS DRS to identify the disorganized phase. It is noted that titanium $L_2$-edge and $L_3$-edge XANES and oxygen K-edge XANES spectroscopies can provide additional data which are consistent with the aforementioned techniques and with differences between the disorganized phase and crystalline titanium dioxide.

Any high resolution transmission electron microscope can be used to image the catalyst or support of this invention. The term "high resolution" implies resolution at the level of atomic lattices. Accordingly, the point to point resolution of the instrument should be at least 2 Å or better. The preferred catalyst and support of this invention exhibits essentially no discernible regular pattern, an image consistent with a disorganized phase. In contrast, a catalyst or support containing crystalline titanium dioxide exhibits images of lattice planes separated by about 3.5 Å for anatase and about 3.25 Å for rutile.

Raman spectroscopy is also sensitive to the presence of crystalline titanium dioxide. Any Raman spectrometer can be used for the analysis; for example, a laser Raman spectrometer having an excitation line at 514.5 nm, 532 nm, and/or 785 nm with a laser power ranging from 90 to 100 mW measured at the sample is acceptable. The anatase phase of titanium dioxide exhibits a characteristic strong, sharp Raman peak at about 147 cm$^{-1}$. The rutile phase of titanium dioxide exhibits peaks at about 448 cm$^{-1}$ and about 612 cm$^{-1}$. The brookite phase of titanium dioxide, which usually occurs only as a natural mineral, exhibits a characteristic peak at about 155 cm$^{-1}$. The rutile and brookite peaks exhibit a lower intensity than the 147 cm$^{-1}$ peak of anatase. In the catalyst of this invention, the Raman peaks for anatase, rutile, and brookite phases are essentially absent. When the catalyst exhibits essentially no detectable peaks at the aforementioned wavenumbers, it is estimated that less than about 0.02 weight percent of the catalyst exists in the form of crystalline titanium dioxide.

The UV-VIS DRS spectrum of the support or catalyst can be obtained on any instrument designed for that purpose, for example, a DRS spectrometer Model UV-3101PC scanning from 200 to 800 nm. The spectrum comprises a convolution of bands due to oxygen to titanium charge transfer in about the 300 nm region, Mie scattering of gold particles in about the 525 nm region, and other bands attributed to scattering by gold particles or absorption by organic species found on used catalyst samples. Deconvolution of the spectra into its separate components can be accomplished by non-linear least squares fitting. The charge transfer region is particularly useful, and its analysis has been previously described by S. Klein et al., in the *Journal of Catalysis*, 163, 489–491 (1996). The fresh catalyst or support of this invention containing disorganized titanium exhibits the charge transfer band at about 310 nm or lower wavelengths. In contrast, a catalyst or support containing crystalline titanium dioxide exhibits the charge transfer band at about 315 nm or higher wavelengths. For example, the pure anatase and rutile phases of titanium dioxide exhibit a peak at 359 nm and 395 nm, respectively.

Titanium K-edge XANES is also useful in distinguishing between the disorganized titanium phase and the anatase and rutile phases of titanium dioxide. Measurement of the XANES spectrum is described hereinbelow. Both anatase and rutile titanium exhibit three peaks in the Ti K-edge XANES. When the instrument is run in transmission mode and calibrated with an internal metallic titanium standard wherein zero energy is set at 4,966.0 eV, anatase and rutile each exhibit three peaks at about +2.9, +5.9, and +8.3 eV. In anatase and rutile the titanium coordination is distorted octahedral. In contrast, the disorganized titanium phase of this invention exhibits substantially a single peak at about +4.6±1.2 eV, preferably, +4.6±0.3 eV. The titanium coordination in the disorganized phase appears to be closer to four or five-fold coordination.

Any silica can be used in the support provided that it allows for an active catalyst composition. The silicas can be amorphous or crystalline. Preferred silicas are surface hydroxylated. Non-limiting examples of suitable silicas include fumed silica, silica gels, precipitated silicas, precipitated silica gels, silicalite and mixtures thereof. Preferably, the surface area of the silica is greater than about 15 m$^2$/g, more preferably, greater than about 20 m$^2$/g, and most preferably, greater than about 25 m$^2$/g. More preferably, the surface area of the silica is less than about 800 m$^2$/g, most preferably, less than about 600 m$^2$/g.

The titanium loading on the silica can be any which gives rise to an active catalyst in the process of this invention. Typically, the titanium loading is greater than about 0.02 weight percent, preferably, greater than about 0.1 weight percent, based on the weight of the silica. Typically, the titanium loading is less than about 20 weight percent, and preferably less than about 10 weight percent, based on the weight of the silica.

The method of depositing the titanium on the silica is important in obtaining the disorganized titanium phase described hereinabove. A description along the lines of the preparation used herein is given by S. Srinivasan et al. in the *Journal of Catalysis*, 131, 260–275 (1991), and by R. Castillo et al., *Journal of Catalysis*, 161, 524–529 (1996), incorporated herein by reference. Generally, the silica support is impregnated with a titanium compound which is reactive with the surface hydroxyls on the silica. Typically, a solution containing a reactive titanium compound is contacted with the silica under mild conditions, such as a temperature between about 0° C. and about 50° C., at about ambient pressure for a time ranging from about 30 minutes to about 24 hours. Non-limiting examples of suitably reactive titanium compounds include titanium alkoxides, such as titanium isopropoxide, titanium propoxide, titanium ethoxide, and titanium butoxide; titanium sulfate, titanium oxysulfate, titanium halides, preferably titanium chloride; as well as titanium carboxylates, preferably titanium oxalate; and organotitanium halides, such as dicyclopentadiene titanium dichloride, and other organotitanocene dichlorides. Preferably, titanium alkoxides are employed. The solvent can be any which solubilizes the reactive titanium compound, for example, aliphatic alcohols, aliphatic and aromatic hydrocarbons, and water where appropriate. After contacting the support with the solution containing the reactive titanium compound, the support is dried at a temperature between about 0° C. and about 150° C., preferably, between about 50° C. and about 150° C., in a vacuum or in a stream of air or an inert gas, such as nitrogen, argon, or helium. Thereafter, the support can be used without calcination or further treatment. Alternatively after drying, the support can be calcined in air or an inert gas, such as nitrogen or helium, to a temperature between about 100° C. and about 800° C., preferably between about 100° C. and about 650° C.

An alternate method of deposition of the titanium is from the gas phase. Volatile titanium compounds, such as titanium chloride, titanium propoxide, or titanium isopropoxide, can be carried through the silica support in a flow of an inert gas such as nitrogen, argon, or helium. The titanium compound can be heated to volatilize or vaporize it into the inert gas stream. The silica support can be heated during the process. Thereafter, the support can be used without calcination or further treatment. Alternatively, the support can be calcined in air or an inert gas, such as nitrogen or helium, to a temperature between about 100° C. and about 800° C., preferably between about 100° C. and about 650° C.

The gold loading on the support can be any amount which yields an active catalyst in the process of this invention. Generally, the gold loading is at least about 0.01, preferably, at least about 0.03, and more preferably at least about 0.05 weight percent, based on the weight of the catalyst. Generally, the loading is lower than about 20, preferably, lower than about 10, and more preferably, lower than about 5.0 weight percent.

The gold component can be deposited or supported on the support by any method known in the art which provides for an active and selective epoxidation catalyst. Non-limiting examples of known deposition methods include impregnation, ion-exchange, and deposition by precipitation. A preferred deposition method is disclosed by S. Tsubota, M. Haruta, T. Kobayashi, A. Ueda, and Y. Nakahara, "Preparation of Highly Dispersed Gold on Titanium and Magnesium Oxide," in *Preparation of Catalysts* V, G. Poncelet, P. A. Jacobs, P. Grange, and B. Delmon, eds., Elsevier Science Publishers B. V., Amsterdam, 1991, p. 695ff., incorporated herein by reference. This method involves contacting the support with an aqueous solution of a soluble gold compound at a temperature and pH sufficient to precipitate the gold compound onto the support. Non-aqueous solutions can also be employed. Thereafter, in the preferred method of this invention which is different from the aforementioned reference, the gold/support composite is not washed or is lightly washed, with preferably no more than about 100 ml wash liquid per gram composite. Then, the composite is calcined or reduced at a temperature sufficient to reduce the gold substantially to metallic gold having an average particle size between about 10 Å and about 500 Å.

Any soluble gold compound can be used. In water, for example, chloroauric acid, sodium chloroaurate, potassium chloroaurate, gold cyanide, potassium gold cyanide, and diethylamine auric acid trichloride are suitable. Typically, the molarity of the soluble gold compound ranges from about 0.001 M to the saturation point of the soluble gold compound, preferably, from about 0.005 M to about 0.5 M. The desired quantity of support is added to the solution, or vice versa; and the pH is adjusted to between about 5 and about 11, preferably, between about 6 and about 9, with any suitable base, such as sodium hydroxide, sodium carbonate, potassium carbonate, cesium hydroxide, and cesium carbonate. Thereafter, the mixture is stirred under air at a temperature between about 20° C. and about 80° C. for a time ranging from about 1 hour to about 24 hours. At the end of this period, the solids are recovered, optionally washed with water, the water optionally containing one or more promoter metal salts, as described hereinbelow, preferably at a pH between about 5 and about 11. Thereafter, the solids are dried under air at a temperature between about 80° C. and about 120° C. The solid is then calcined under air, or calcined in a reducing atmosphere, such as hydrogen, or heated in an inert atmosphere, such as nitrogen, at a temperature between about 250° C. and about 800° C., preferably between about 350° C. and about 750° C., for a time from about 1 to about 24 hours to form the catalyst of this invention.

Optionally, the catalyst of this invention can contain a promoter metal or a combination of promoter metals. Any metal ion having a valence between +1 and +7 which enhances the productivity of the catalyst in the oxidation process of this invention can be employed as a promoter metal. Factors contributing to increased productivity of the catalyst include increased conversion of the olefin, increased selectivity to the olefin oxide, decreased productivity to water, and increased catalyst lifetime. Non-limiting examples of suitable promoter metal include the metals of Groups 1 through 12 of the Periodic Table of the Elements, as well as the rare earth lanthanides and actinides, as referenced in the *CRC Handbook of Chemistry and Physics*, 75$^{th}$ ed., CRC Press, 1994. Preferably, the promoter metal is selected from Group 1 metals of the Periodic Table including lithium, sodium, potassium, rubidium, and cesium; from Group 2 metals, including beryllium, magnesium, calcium, strontium, and barium; from the lanthanide rare earth metals, including cerium, praseodymium, neodymium, promethium, samarium, europium, gadolinium, terbium, dysprosium, holmium, erbium, thulium, ytterbium, and lutetium; and the actinide metals, specifically, thorium and uranium. More preferably, the promoter metal is selected from magnesium, calcium, barium, erbium, lutetium, lithium, potassium, rubidium, cesium, and combinations thereof. Preferably, the promoter metal excludes palladium, and more preferably, the promoter metal excludes a Group VIII metal, specifically, iron, cobalt, nickel, ruthenium, rhodium, palladium, osmium, iridium, and platinum. As used herein, the word "excludes" means that the total concentration of the Group VIII metal is less than about 0.01 weight percent, preferably, less than about 0.005 weight percent, based on the total catalyst composition.

If one or more promoter metals are used, then the total quantity promoter metal(s) generally is greater than about 0.01, preferably, greater than about 0.10, and more preferably, greater than about 0.15 weight percent, based on the total weight of the catalyst. The total quantity of promoter metal(s) is generally less than about 20, preferably, less than about 15, and more preferably, less than about 10 weight percent, based on the total weight of the catalyst.

The titanium ions, gold, and promoter metal ion(s) can be deposited onto the silica in any order. The titanium ions can be dispersed first, and thereafter the gold and promoter metal ions can be deposited. Alternatively, the gold and promoter metal ions can be deposited first, and thereafter the titanium ions dispersed. The promoter metal(s) can be deposited onto the support simultaneously with the gold particles, or alternatively, in a separate deposition step either before or after the gold is deposited. Alternatively, the promoter metal can be deposited onto a precursor form of the catalyst before the titanium is added, or after it is added, or simultaneously with the titanium. Typically, the promoter metal is deposited from an aqueous or organic solution containing a soluble promoter metal salt. Any salt of the promoter metal which has adequate solubility can be used; for example, the promoter metal nitrates, halides, and carboxylates, preferably, the nitrates, are suitable. A variety of organic solvents can be used, including, alcohols, esters, ketones, and aliphatic and aromatic hydrocarbons. Ordinarily, the support is contacted with the solution of the promoter metal salt under conditions which are similar to those used for contacting the support with the gold solution. After the promoter metal is deposited, washing is optional, but if done to excess, can leach at least a portion of the promoter metal out of the catalyst. Afterwards, calcination under air or under a reducing atmosphere or heating in an inert gas is conducted in a manner similar to that described hereinabove for the gold deposition.

Optionally, the catalyst of this invention can be extruded with, bound to, or supported on a second support, such as silica, alumina, an aluminosilicate, magnesia, titania, carbon, or mixtures thereof. The second support may function to improve the physical properties of the catalyst, such as, the strength or attrition resistance, or to bind the catalyst particles together. Generally, the quantity of second support ranges from about 0 to about 95 weight percent, based on the combined weight of the catalyst and second support. It is noted that although the catalyst of this invention can be physically mixed or extruded with titania or bound to titania as a second support, in a preferred embodiment the catalyst is substantially free of the anatase phase of titania, more preferably, substantially free of crystalline titania, as noted hereinabove. If titania is used as a second support, however, note that its presence may interfere with the analytical identification of the disorganized phase of the catalyst. In this instance especially, analysis for the disorganized phase should be made in the absence of the second support.

The process of this invention can be conducted in a reactor of any conventional design suitable for gas or liquid phase processes. These designs broadly include batch, fixed-bed, transport bed, fluidized bed, moving bed, trickle bed, and shell and tube reactors, as well as continuous and intermittent flow and swing reactor designs. The olefin, hydrogen, and oxygen can be contacted together. Alternatively, the process can be conducted step-wise wherein the catalyst is first contacted with oxygen and thereafter the oxygenated catalyst is contacted with a mixture of propylene and hydrogen. Preferably, the process is conducted in the gas phase, and the reactor is designed with heat transfer features for the removal of the heat produced. Preferred reactors designed for these purposes include fixed-bed, shell and tube, fluidized bed, and moving bed reactors, as well as swing reactors constructed from a plurality of catalyst beds connected in parallel and used in an alternating fashion.

The process conditions for the direct oxidation described herein can vary considerably over a nonflammable and flammable regime. It is beneficial, however, to recognize the conditions which distinguish between nonflammable and flammable mixtures of the olefin, hydrogen, and oxygen. Accordingly, a phase diagram can be constructed or consulted which for any given process temperature and pressure shows the flammable and non-flammable range of reactant compositions, including the diluent, if used. The more preferred reactant mixtures specified hereinabove are believed to lie outside the flammable regime when the process is operated at the more preferred temperatures and pressures specified hereinbelow. Nevertheless, operation within the flammable regime is possible, as designed by one skilled in the art.

Usually, the process is conducted at a temperature which is greater than about ambient, taken as 20° C., preferably, greater than about 70° C., more preferably greater than about 120° C. Usually, the process is conducted at a temperature less than about 250° C., preferably less than about 225° C., more preferably, less than about 200° C. Preferably, the pressure ranges from about atmospheric to about 400 psig (2758 kPa), more preferably, from about 150 psig (1034 kPa) to about 250 psig (1724 kPa).

In flow reactors the residence time of the reactants and the molar ratio of reactants to catalyst will be determined by the space velocity. For a gas phase process the gas hourly space velocity (GHSV) of the olefin can vary over a wide range, but typically is at least about 10 ml olefin per ml catalyst per hour ($hr^{-1}$), preferably greater than about 100 $hr^{-1}$, and more preferably, greater than about 1,000 $hr^{-1}$. Typically, the GHSV of the olefin is less than about 50,000 $hr^{-1}$, preferably, less than about 35,000 $hr^{-1}$, and more preferably, less than about 20,000 $hr^{-1}$. Likewise, for a liquid phase process the weight hourly space velocity (WHSV) of the olefin component can vary over a wide range, but typically is greater than about 0.01 g olefin per g catalyst per hour ($hr^{-1}$), preferably, greater than about 0.05 $hr^{-1}$, and more preferably, greater than about 0.1 $hr^{-1}$. Typically, the WHSV of the olefin is less than about 100 $hr^{-1}$, preferably, less than about 50 $hr^{-1}$, and more preferably, less than about 20 $hr^{-1}$. The gas and weight hourly space velocities of the oxygen, hydrogen, and diluent components can be determined from the space velocity of the olefin taking into account the relative molar ratios desired.

When an olefin having at least three carbon atoms is contacted with oxygen in the presence of hydrogen and the catalyst described herein-above, the corresponding olefin oxide (epoxide) is produced in good productivity. The most preferred olefin oxide produced is propylene oxide.

The conversion of olefin in the process of this invention can vary depending upon the specific process conditions employed, including the specific olefin, temperature, pressure, mole ratios, and form of the catalyst. For the purposes of this invention the term "conversion" is defined as the mole percentage of olefin which reacts to form products. Generally, the conversion increases with increasing temperature and pressure and decreases with increasing space velocity. Typically, an olefin conversion of greater than about 0.05 mole percent is achieved. Preferably, the olefin conversion is greater than 0.2 mole percent, and more preferably, greater than about 1.5 mole percent.

The selectivity to olefin oxide can vary depending upon the specific process conditions employed. For the purposes of this invention, the term "selectivity" is defined as the mole percentage of reacted olefin which forms a particular product, desirably the olefin oxide. Generally, the selectivity to olefin oxide will decrease with increasing temperature and increase with increasing space velocity. The process of this invention produces olefin oxides in unexpectedly high selectivity. Typically the selectivity to olefin oxide is greater than about 70, preferably, greater than about 80, and more preferably, greater than about 90 mole percent. A selectivity to propylene oxide of greater than about 97 mole percent is obtained at 50° C. Even at 140° C. the selectivity to propylene oxide is surprisingly high, between about 85 and 95 mole percent.

The productivity of the catalyst, measured as millimoles of propylene oxide per gram catalyst per hour (mmol/g cat-hr), is generally greater than about 0. 1, preferably, greater than about 0.4, and more preferably, greater than about 0.9 mmol/g cat-hr.

Advantageously, the hydrogen efficiency in the process of this invention is satisfactory. Some additional hydrogen may be burned directly to form water. Accordingly, it is desirable to achieve a water/olefin oxide molar ratio as low as possible. In the process of this invention, the water/olefin oxide molar ratio is typically greater than about 2/1, but less than about 15/1, and preferably, less than about 10/1, and more preferably, less than about 7/1.

The catalyst of this invention exhibits evidence of a long lifetime. The term "lifetime" as used herein refers to the time measured from the start of the oxidation process to the point at which the catalyst after regeneration has lost sufficient activity so as to render the catalyst useless, particularly commercially useless. As evidence of its long lifetime, the catalyst remains active for long periods of time with little deactivation. Typically, a run time greater than about 20 hours without catalyst deactivation has been achieved in a fixed bed reactor. The preferred run time between regenerations will depend upon the reactor design and may range from minutes for transport bed reactors to several months for fixed bed reactors. As further evidence of its longevity, the catalyst of this invention can be regenerated through multiple cycles without substantial loss in catalyst activity or selectivity.

When its activity has decreased to an unacceptably low level, the catalyst of this invention can be easily regenerated. Any catalyst regeneration method generally known to those skilled in the art can be used with the catalyst of this invention provided that the catalyst is reactivated for the oxidation process described herein. One suitable regeneration method comprises heating the deactivated catalyst at a temperature between about 150° C. and about 500° C. under an atmosphere of a regeneration gas containing hydrogen and/or oxygen and optionally an inert gas. A preferred regeneration temperature lies between about 200° C. and about 400° C. The amounts of hydrogen and/or oxygen in the regeneration gas can be any which effectively regenerates the catalyst. Preferably, the hydrogen and/or oxygen comprises from about 2 to about 100 mole percent of the regeneration gas. Suitable inert gases are non-reactive and include, for example, nitrogen, helium, and argon. The time during which the catalyst is regenerated can range from as short as about 2 minutes to as long as several hours, for example, about 20 hours at the lower regeneration temperatures. In an alternative embodiment, water is beneficially added to the regeneration gas, in an amount preferably ranging from about 0.01 to about 100 mole percent.

The invention will be further clarified by a consideration of the following examples, which are intended to be purely exemplary of the use of the invention. Other embodiments of the invention will be apparent to those skilled in the art from a consideration of this specification or practice of the invention as disclosed herein. Unless otherwise noted, all percentages are given on a weight percent basis.

The Ti K-edge XANES data were collected on beam line X19A at the National Synchrotron Light Source (NSLS). The monochromator is a NSLS boomerang-type flat crystal monochromator with Si(111) crystals. Mirrors were used to focus the beam both horizontally and vertically resulting in an approximately 1 mm×1 mm beam size at the focal position inside an experimental hutch. A 0.4 mm white beam slit was used to enhance the resolution. The synchrotron operated with an electron energy of 2.583 GeV with beam currents ranging from 100 to 300 mA. Higher harmonics in the beam were rejected by detuning the second Si(111) monochromator crystals to 75 percent of the maximum intensity. The incident beam intensity was monitored with an ion chamber which was integral to the beam pipe and continuously purged with helium gas. The X-ray absorption spectra were recorded as fluorescence yield spectra using a Lytle in situ cell flushed with nitrogen gas. No fluorescence filter was used although Soller slits were in place. The sample chamber was placed close to the end of the beam pipe to minimize air absorption and scattering at the relatively low energy of the Ti K-edge (4.996 keV). All of the catalyst samples were measured using the Lytle in situ cell arrangement with the catalyst powders pressed into self-supporting 1 inch diameter wafers (typical parameters used: 0.3–0.4 g catalyst, 3500 Kg for 5 min.) The instrument was run in transmission mode. Titanium foil was used to calibrate the energy as follows. The first maximum of the first derivative of the metallic titanium K-edge peak was set at 4,966.0 eV. Measurement of the sample energy was made relative to the 4,966.0 eV calibration point, which was taken as zero energy.

As a correlation with the Raman measurement technique, some samples were heated at 500° C. in a 20 volume percent mixture of oxygen in helium prior to XANES analysis. Due to the location of the thermocouple in the Lytle cell, it is believed that the actual catalyst temperature could be as much as 50° C. lower than the set point. After treatment the cell was purged with pure helium to minimize absorption of the X-rays by oxygen.

EXAMPLE 1

A support comprising titanium dispersed on silica is prepared following the procedure of S. Srinivasan et al. as described in the *Journal of Catalysis* 131, 260–275 (1991), with the exception that the titanium-silica composite is not heated to a temperature greater than 200° C. . Cabosil silica is used. Neutron activation analysis (NAA) of the support gives 2.84 percent Ti and 44 percent silicon. The surface area of the support is 300 $m^2/g$. The support shows no crystalline phases of titania as detected by Raman. Ti K-edge XANES exhibits one peak at +4.8 eV. Gold is deposited on the support as follows: Chloroauric acid (0.04 g) is dissolved in water (100 ml). The pH of the solution is adjusted to 7.5 at 80° C. with sodium carbonate. Then the support (1.0 g) is added and stirred. The mixture is cooled to room temperature and magnesium nitrate (0.1 g) is added. The mixture is stirred overnight at room temperature. A solid material is filtered and washed once with water. The solid is calcined in air by heating to 400° C. over 8 hr. and holding thereat for 3 hr. Afterwards, the solid is cooled to room temperature.

Composition by NAA: 2.86 percent Ti, 45.0 percent Si, 0.25 percent Au, 0.54 percent Mg, and 0.33 percent Na. HR-TEM exhibits no organized structure indicative of crystalline titanium dioxide. Raman spectrum exhibits no peaks for crystalline titanium dioxide. Average gold particle size is 27 Å, as measured by HR-TEM.

The catalyst (1 g) is loaded into a 10 cc fixed-bed, continuous flow reactor with feeds of helium, oxygen, hydrogen, and propylene. Feedstream composition is 30 mole percent propylene, 7 mole percent hydrogen, 7 mole percent oxygen, the balance being helium. The propylene/hydrogen molar ratio is 4.2; the propylene/oxygen ratio is 4.2; the hydrogen/oxygen ratio is 1.0. Propylene, oxygen and helium are used as pure streams; hydrogen is mixed with helium in a 20 $H_2$/80 He (v/v) mixture. Total flow rate is 2400 cc/hr. Pressure is atmospheric; reactor temperature 135° C. Products are analyzed using on-line gas chromatography (Chrompak™ Porapak™ S, 25 m) and on-line mass spectrometry.

The catalyst exhibits a 2 mole percent propylene conversion at 92 mole percent selectivity to propylene oxide for 20 hr at 145° C. The maximum conversion is 3.3 percent at 92 percent selectivity to propylene oxide, the only detectable byproducts being carbon dioxide and water. The catalyst produces greater than 0.58 mmol/g cat-hr for 20 hr with the peak at 1.0 mmol/g cat-hr. The outlet propylene oxide concentration is greater than 0.6 mole percent for 20 hr with the peak at 1 percent.

EXAMPLE 2

Silica (Cabot Cab-O-Sil-EH5 fumed silica) was wetted, dried at 110° C., crushed and sieved through 60 mesh, and then calcined at 300° C. In a glovebox, titanium isopropoxide (8.2 g) was dissolved in isopropanol (128 g). The titanium solution was added to the silica (63.1 g) in a flask and shaken for 1 hr. The flask was attached to a rotary evaporator and the solvent was removed at room temperature under vacuum. The residue was heated in the rotary evaporator to 100° C. and held for 1 hr under vac uum yielding a support of this invention.

Chloroauric acid (2.0687 g; 49.28 percent Au; Alfa Aesar) was dissolved in water (3200 cc) a nd the solution was heated to 70° C. The pH was adjusted to 7.5 with sodium carbonate. The support (44.2 g) was added with vigorous stirring. The pH was adjusted to 7.5 with sodium carbonate. The mixture was cooled to room temperature overnight, and the pH drifted to about 8. The solids were filtered and washed with water (600 ml) of pH 7.5 (containing sodium carbonate). The solids were then dried at 100° C. for 4 hr; then heated from 100° C to 500° C. in 8 hr and held at 500aC for 5 hr to yield a catalyst of this invention.

Composition by NAA: 44.3 percent Si, 2.16 percent Ti, 0.33 percent Au, 0.59 percent Na. Raman spectrum exhibited no evidence of crystalline titanium dioxide. UV-VIS DRS (fresh catalyst) exhibited a peak at 298.0 nm. HR-TEM exhibited no evidence of crystalline titanium dioxide. Average gold particle size was 63 Å. Ti K-edge XANES exhibited one peak at +4.60 eV.

The catalyst (2.84 g, 10 cc) was loaded into a fixed bed reactor and tested in the oxidation of propylene. Feed composition was 30 percent propylene, 10 percent oxygen, 12 percent hydrogen, and balance helium, on a mole basis, at a total flow rate of 150 cc/min. The activity is shown in Table 1.

TABLE 1

| | % PP Conv / % PO Sel ($H_2O$/PO Ratio)[a,b] | | |
|---|---|---|---|
| T (°C.) | Time (hr) | Example 2 | Example 3 |
| 100 | 0.5 | 0.62/91.3 (6.71) | 0.14/94.6 (17.04) |
| 120 | 1 | 0.56/90.5 (8.28) | 0.26/89.6 (11.35) |
| 130 | 1.5 | 0.58/88.5 (10.94) | 0.26/86.1 (13.83) |
| 130 | 3.5 | 0.42/88.9 (15.91) | 0.26/86.2 (16.52) | a. % PP conv = mole percentage propylene conversion, % PO Sel = mole percentage selectivity to propylene oxide, $H_2O$/PO = molar ratio of water to propylene oxide
b. Feed: 30% PP, 10% oxygen, 12% hydrogen, balance helium, total flow rate 150 cc/min, atmospheric pressure It is seen that the catalyst of Example 2 achieved a high selectivity to propylene oxide at good propylene conversion and hydrogen efficiency.

EXAMPLE 3

The support (12.0 g) prepared in Example 2 was calcined in air by heating at 100° C. for 2 hr, then heating from 100° C. to 500° C. in 8 hr, and holding at 500° C. for 5 hr. Chloroauric acid (0.3933 g) was dissolved in water (900 cc) and heated to 70° C. The pH was adjusted to 7.5 with sodium carbonate. The support (8.0 g) was added with vigorous stirring. and the pH was adjusted to 7.5 with sodium carbonate. The mixture was cooled to room temperature and the pH drifted to about 8. The solids were filtered and washed with water (100 ml) of pH 7.5 (containing sodium carbonate). The solids were dried at 100C for 4 hr. then heated from 100° C to 500° C. in 8 hr, and held at 500° C. for 5 hr yield a catalyst of this invention.

Composition by NAA: 44.3 percent Si, 2.10 percent Ti, 0.166 percent Au, 0.59 percent Na. Raman spectrum exhibited no peaks for crystalline titanium dioxide. UV-VIS DRS (fresh catalyst) exhibited a peak at 296.6 nm. Ti K-edge XANES exhibited one peak at +4.60 eV.

The catalyst (10 cc, 2.37 g) was tested in the oxidation of propylene as described in Example 2 with the results shown in Table 1. It is seen that the catalyst of Example 3 achieved a high selectivity to propylene oxide at good conversion and hydrogen efficiency; however, calcination of the support at 500° C. prior to gold deposition lowered the catalyst productivity as compared with Example 2 wherein the support was not calcined.

EXAMPLE 4

In a glovebox, titanium tetrachloride (1.71 g) was dissolved in hexane (35 g). The resulting solution was added to silica (16.46 g, 40/60 mesh of Cabot Cab-O-Sil-EH5 fumed silica which had previously been wetted, dried at 110° C., and calcined at 400° C.). The mixture was shaken and allowed to sit for 15 min. Solvent and volatiles were removed on a rotary evaporator at room temperature. The residue was heated to 80° C. under vacuum, then cooled to room temperature to yield a support of this invention. A gold solution was made by dissolving chloroauric acid (0.3030 g) in distilled water (700 cc) and heating to 70° C. The pH of the gold solution was adjusted to 7.5 with sodium carbonate and the solution was cooled to room temperature. Magnesium nitrate (0.7017 g) was added to the solution. The support (one-half of the support sample) was added quickly with vigorous stirring at room temperature. The pH was readjusted to 7.5 with sodium carbonate. The mixture was stirred at room temperature overnight, and then the solids were filtered. The solids were rinsed with a solution (100 cc) prepared by dissolving magnesium nitrate (0.125 g) in water (800 cc) and adjusting the pH to 7.5 with sodium carbonate. The solids were rinsed, dried at 100° C. for 2 hr in air, calcined in air from 100° C. to 400° C. in 8 hr, and held at 400° C. for 5 hr yielding a catalyst of this invention.

Composition by NAA: 41.2 percent Si, 2.54 percent Ti, 0.78 percent Au, 0.37 percent Na, 0.43 percent Mg. Raman exhibited no peaks for crystalline titanium dioxide. UV-VIS DRS (fresh catalyst) exhibited a peak at 301.1 nm.

The catalyst (1.48 g) was tested in the oxidation of propylene with oxygen with the results shown in Table 2.

TABLE 2

| | Conv PP / Sel PO ($H_2O$/PO Ratio)[a,b] | |
|---|---|---|
| T (°C.) | Time (hr) | Example 4 |
| 80 | 0.75 | 0.14/86.6 (17.3) |
| 110 | 1.5 | 0.23/88.6 (8.94) |
| 130 | 2.0 | 0.21/82.7 (10.83) | a. % PP conv = mole percentage propylene conversion, % PO Sel = mole percentage selectivity to propylene oxide, $H_2O$/PO = molar ratio of water to propylene oxide
b. Feed: 30% PP, 10% oxygen, 11% hydrogen, balance helium, total flow rate 150 cc/min, atmospheric pressure It is seen that a catalyst containing gold and magnesium on a support prepared from titanium tetrachloride is active and selective in the direct oxidation of propylene to propylene oxide.

EXAMPLE 5

In a glovebox titanium ethoxide [1.14 g, Ti(O-Et)$_4$ (~20 percent Ti in ethanol from Aldrich] was dissolved in hexane (20.8 g). The resulting solution was added to silica (11.1 g, 40/60 mesh of Cabot Cab-O-Sil-EH5 fumed silica). The silica had previously been wetted and dried at 110° C., and calcined at 500° C. The mixture was shaken and allowed to sit for 10 min. The solvent and volatiles were removed on a rotary evaporator at room temperature for 1 hr in vacuo. Then, the residue was heated to 100° C. under vacuum, rotated at 100° C. for about 1 hr, and cooled to room temperature to obtain a support of this invention.

A gold solution was made by dissolving chloroauric acid (0.1040 g) in water (400 cc) and heating to 70° C. The pH was adjusted to 7.5 with sodium carbonate. The support (5.017 g) was added quickly and stirred vigorously at 70° C. The pH was readjusted to 7.5 with sodium carbonate. The mixture was stirred at 70° C. for 1 hr while keeping the pH at 7.5, and then cooled to room temperature. The solids were filtered. The solids were added to water (200 cc) at pH 7.5 (from $Na_2CO_3$) and stirred for 5 min. The solids were filtered, dried at room temperature for 1 hr by pulling air through the solids on the filter frit. The material was calcined in air from room temperature to 100° C. in 1 hr; held at 100° C. for 1 hr; then heated in 8 hr to 400° C. and held at 400° C. for 4 hr yielding a catalyst of this invention.

Composition by NAA: 0.106 percent Au, 0.48 percent Na, 1.96 percent Ti, 43.2 percent Si; no magnesium detected. No crystalline titanium dioxide was detected by Raman (532 nm excitation) or HR-TEM. Average gold particle size was 15 Å. The UV-VIS DRS (fresh catalyst) exhibited a peak at 309.9 nm. Ti K-edge XANES exhibited one peak at +4.70 eV.

The catalyst (2.01 g, 7.5 cc) was tested in the oxidation of propylene with oxygen with the results shown in Table 3. The used catalyst was regenerated a first time as follows. The catalyst was flushed with a mixture of oxygen (10 mole percent) in helium until no propylene was seen on a mass spectrometer. The catalyst was then heated from 140° C. to 350° C. in 45 min in the oxygen/helium mixture at a flow of 150 cc/min, then held at 350° C. for 2 hr. The catalyst was cooled to 120° C. in the gas mixture. The regenerated catalyst was tested in the oxidation process with the results shown in Table 3. The catalyst was regenerated a second time as follows. The catalyst was flushed with a mixture of oxygen (10 mole percent) in helium until no propylene was seen on a mass spectrometer. The catalyst was heated from 120° C. to 350° C. in 1 hr in the oxygen/helium mixture at a flow of 150 cc/min, then heated to 370° C. in about 15 min, and held at 370° C. for 1 hr. The catalyst was cooled to 350° C. in the oxygen/helium mixture and held at 350° C. for 4 hr. The catalyst was cooled to 120° C. in the oxygen/helium mixture and then retested in the oxidation process with the results shown in Table 3.

TABLE 3

| % PO Sel / % PP Conv ($H_2O$/PO)[a,b] | | | | |
|---|---|---|---|---|
| Time (hr) | T (°C.) | % PO Sel. | % PP Conv. | $H_2O$/PO |
| 0.1 | 100 | 96.0 | 0.156 | 7.02 |
| 0.9 | 100 | 96.4 | 0.213 | 3.79 |
| 1.7 | 120 | 94.4 | 0.293 | 3.67 |
| 2.5 | 120 | 94.1 | 0.245 | 4.54 |
| 3.3 | 120 | 94.3 | 0.233 | 4.30 |
| 14.5 | 120 | 94.2 | 0.138 | 6.37 |
| 16.9 | 140 | 91.5 | 0.254 | 6.96 |
| After first regeneration: | | | | |
| 0.1 | 120 | 92.1 | 0.257 | 7.66 |
| 0.9 | 120 | 94.1 | 0.259 | 4.44 |

TABLE 3-continued

| % PO Sel / % PP Conv ($H_2O$/PO)[a,b] | | | | |
|---|---|---|---|---|
| Time (hr) | T (°C.) | % PO Sel. | % PP Conv. | $H_2O$/PO |
| 1.7 | 120 | 93.8 | 0.194 | 5.08 |
| 15.3 | 120 | 94.4 | 0.145 | 6.28 |
| After second regeneration: | | | | |
| 0.1 | 120 | 89.8 | 0.185 | 10.00 |
| 0.9 | 120 | 93.5 | 0.254 | 5.58 |
| 1.7 | 120 | 94.0 | 0.215 | 5.60 |
| 2.5 | 120 | 94.0 | 0.215 | 5.44 |
| 4.1 | 120 | 94.5 | 0.184 | 5.25 |
| 13.7 | 120 | 93.3 | 0.112 | 7.39 |
| 15.3 | 140 | 88.8 | 0.206 | 8.08 | a. % PP conv = mole percentage propylene conversion, % PO Sel = mole percentage selectivity to propylene oxide, $H_2O$/PO = molar ratio of water to propylene oxide
b. Feed: 30% PP, 10% oxygen, 11% hydrogen, balance helium, total flow 150 cc/min, atmospheric pressure.

It is seen that the catalyst of Example 5 containing gold on a support prepared with titanium ethoxide is an active catalyst for the direct oxidation of propylene to propylene oxide.

EXAMPLE 6

A gold solution was made by dissolving chloroauric acid (0.1055 g) in water (400 cc) and heating to 70° C. The pH was adjusted to 7.5 with sodium carbonate. The support (5.035 g) of Example 5 was added quickly and stirred vigorously at 70° C. The pH was readjusted to 7.5 with sodium carbonate. Magnesium nitrate (0.50 g) was added to the solution and the pH adjusted with sodium carbonate. The mixture was stirred at 70° C. for 1 hr while keeping the pH at 7.5, and then cooled to room temperature. The solids were filtered. The solids were added to water (200 cc) at pH 7.5 (from $Na_2CO_3$) and stirred for 5 min. The solids were filtered, dried at room temperature for 1 hr by pulling air through the solids on the filter frit. The material was calcined in air from room temperature to 100° C. in 1 hr; held at 100° C. for 1 hr; then heated in 8 hr to 400° C. and held at 400° C. for 4 hr yielding a catalyst of this invention.

Composition by NAA: 0.207 percent Au, 0.53 percent Mg, 0.17 percent Na, 1.94 percent Ti, 42.0 percent Si. No crystalline titanium dioxide was detected by Raman (532 excitation). The UV-VIS DRS (fresh catalyst) exhibited a peak at 306.4 nm. Titanium K-edge XANES exhibited a single peak at +4.67 eV.

The catalyst (2.01 g, 7.5 cc) was tested in the oxidation of propylene with oxygen with the results shown in Table 4. The catalyst was regenerated twice as described in Example 5 and retested in the oxidation process with the results shown in Table 4.

TABLE 4

| % PO Sel / % PP Conv ($H_2O$/PO)[a,b] | | | | |
|---|---|---|---|---|
| Time (hr) | T (°C.) | % PO Sel. | % PP Conv. | $H_2O$/PO |
| 0.3 | 100 | 97.5 | 0.363 | 5.15 |
| 1.1 | 100 | 97.8 | 0.306 | 4.77 |
| 1.9 | 120 | 91.7 | 0.409 | 6.18 |
| 2.7 | 120 | 94.1 | 0.345 | 6.71 |
| 3.5 | 120 | 91.9 | 0.334 | 6.89 |
| 14.7 | 120 | 94.2 | 0.172 | 9.65 |
| 17.1 | 140 | 84.3 | 0.279 | 12.17 |

TABLE 4-continued

% PO Sel / % PP Conv (H$_2$O/PO)[a,b]

| Time (hr) | T (°C.) | % PO Sel. | % PP Conv. | H$_2$O/PO |
|---|---|---|---|---|
| After first regeneration: | | | | |
| 0.3 | 120 | 91.5 | 0.461 | 6.91 |
| 1.1 | 120 | 93.9 | 0.354 | 6.88 |
| 1.9 | 120 | 92.9 | 0.301 | 7.62 |
| 15.5 | 120 | 92.9 | 0.153 | 10.18 |
| After second regeneration: | | | | |
| 0.3 | 120 | 91.9 | 0.549 | 6.74 |
| 1.1 | 120 | 91.3 | 0.390 | 7.42 |
| 1.9 | 120 | 93.2 | 0.315 | 8.00 |
| 2.7 | 120 | 92.8 | 0.252 | 8.72 |
| 4.3 | 120 | 93.4 | 0.244 | 8.46 |
| 13.9 | 120 | 93.9 | 0.167 | 11.39 |
| 15.5 | 140 | 82.8 | 0.276 | 13.80 | a. % PP conv = mole percentage propylene conversion, % PO Sel = mole percentage selectivity to propylene oxide, H$_2$O/PO = molar ratio of water to propylene oxide
b. Feed: 30% PP, 10% oxygen, 11% hydrogen, balance helium, total flow 150 cc/min, atmospheric pressure.

It is seen that the catalyst of Example 6 containing gold and magnesium on a support prepared from titanium ethoxide achieved a high selectivity to propylene oxide, good propylene conversion, and high hydrogen efficiency.

EXAMPLE 7

A support was prepared as in Example 5 with the exception that titanium isopropoxide (1.34 g) dissolved in isopropanol (24.0 g) was used in place of titanium ethoxide dissolved in hexane. Gold was deposited on the support as in Example 5 with the exception that chloroauric acid (0.1050 g) was used with the support (5.045 g).

Composition by NAA: 0.098 percent Au, 0.43 percent Na, 1.89 percent Ti, 42.0 percent Si, ; Mg not detected. No crystalline titanium dioxide was detected by Raman (532 excitation) and HR-TEM. Average gold particle size was 15 Å. The UV-VIS DRS (fresh catalyst) exhibited a peak at 301.5 nm. Titanium K-edge XANES exhibited a single peak at +4.42 eV.

The catalyst (2.0 g, 7.5 cc) was tested in the oxidation of propylene with oxygen with the results shown in Table 5. The used catalyst was regenerated twice as in Example 5 and retested in the oxidation process with the results shown in Table 5.

TABLE 5

% PO Sel / % PP Conv (H$_2$O/PO)[a,b]

| Time (hr) | T (°C.) | % PO Sel. | % PP Conv. | H$_2$O/PO |
|---|---|---|---|---|
| 0.5 | 100 | 97.3 | 0.292 | 3.68 |
| 1.3 | 100 | 96.5 | 0.226 | 3.55 |
| 2.1 | 120 | 95.3 | 0.327 | 3.98 |
| 2.9 | 120 | 95.5 | 0.298 | 3.84 |
| 3.7 | 120 | 95.2 | 0.281 | 3.95 |
| 14.9 | 120 | 94.9 | 0.182 | 4.82 |
| 17.3 | 140 | 92.6 | 0.309 | 5.49 |
| After first regeneration: | | | | |
| 0.5 | 120 | 92.2 | 0.366 | 3.85 |
| 1.3 | 120 | 94.9 | 0.279 | 4.07 |
| 2.1 | 120 | 94.8 | 0.245 | 4.27 |
| 15.7 | 120 | 94.4 | 0.146 | 6.59 |

TABLE 5-continued

% PO Sel / % PP Conv (H$_2$O/PO)[a,b]

| Time (hr) | T (°C.) | % PO Sel. | % PP Conv. | H$_2$O/PO |
|---|---|---|---|---|
| After second regeneration: | | | | |
| 0.5 | 120 | 90.7 | 0.359 | 4.29 |
| 1.3 | 120 | 94.2 | 0.267 | 4.69 |
| 2.1 | 120 | 94.7 | 0.236 | 5.05 |
| 2.9 | 120 | 94.9 | 0.213 | 4.86 |
| 4.5 | 120 | 94.1 | 0.196 | 5.69 |
| 14.1 | 120 | 93.9 | 0.143 | 7.36 |
| 15.7 | 140 | 91.7 | 0.257 | 6.13 | a. % PP conv = mole percentage propylene conversion, % PO Sel = mole percentage selectivity to propylene oxide, H$_2$O/PO = molar ratio of water to propylene oxide
b. Feed: 30% PP, 10% oxygen, 11% hydrogen, balance helium, total flow 150 cc/min, atmospheric pressure.

It is seen that the catalyst of Example 7 containing gold on a support prepared from titanium isopropoxide achieved excellent selectivity to propylene oxide, good propylene conversion, and excellent hydrogen efficiency.

EXAMPLE 8

Gold was deposited onto the support of Example 7 (5.045 g) in the manner described in Example 6. Chloroauric acid (0.1044 g) was used to prepare the gold solution, and magnesium nitrate (0.49 g) was added to the mixture.

Composition by NAA: 0.210 percent Au, 0.48 percent Mg, 0.14 percent Na, 1.85 percent Ti, 41.2 percent Si. No crystalline titanium dioxide was detected by Raman (532 excitation). The DRS (fresh catalyst) exhibited a peak at 298.1 nm. Ti K-edge XANES exhibited a single peak at +4.66 eV.

The catalyst (2.00 g, 7.5 cc) was tested in the oxidation of propylene with oxygen with the results shown in Table 6. The used catalyst was regenerated twice in the manner described in Example 5 and retested in the oxidation process with the results shown in Table 6.

TABLE 6

% PO Sel / % PP Conv (H$_2$O/PO)[a,b]

| Time (hr) | T (°C.) | % PO Sel. | % PP Conv. | H$_2$O/PO |
|---|---|---|---|---|
| 0.7 | 100 | 96.5 | 0.452 | 4.12 |
| 1.5 | 100 | 96.1 | 0.374 | 4.55 |
| 2.3 | 120 | 91.4 | 0.482 | 6.48 |
| 3.1 | 120 | 90.6 | 0.366 | 6.53 |
| 3.9 | 120 | 92.6 | 0.324 | 6.65 |
| 15.1 | 120 | 92.8 | 0.209 | 8.29 |
| 17.5 | 140 | 85.2 | 0.326 | 12.14 |
| After first regeneration: | | | | |
| 0.7 | 120 | 90.3 | 0.510 | 6.44 |
| 1.5 | 120 | 89.8 | 0.398 | 7.00 |
| 2.3 | 120 | 92.2 | 0.344 | 7.78 |
| 15.9 | 120 | 92.5 | 0.192 | 9.80 |
| After second regeneration: | | | | |
| 0.7 | 120 | 90.3 | 0.504 | 7.10 |
| 1.5 | 120 | 92.0 | 0.400 | 7.24 |
| 2.3 | 120 | 89.1 | 0.368 | 7.59 |
| 3.1 | 120 | 88.8 | 0.323 | 7.81 |
| 4.7 | 120 | 92.7 | 0.271 | 8.57 |
| 14.3 | 120 | 91.9 | 0.198 | 9.73 |
| 15.9 | 140 | 77.8 | 0.336 | 12.68 |

TABLE 6-continued

% PO Sel / % PP Conv (H₂O/PO)$^{a,b}$

| Time (hr) | T (°C.) | % PO Sel. | % PP Conv. | H₂O/PO |
|---|---|---|---|---| a. % PP conv = mole percentage propylene conversion, % PO Sel = mole percentage selectivity to propylene oxide, H₂O/PO = molar ratio of water to propylene oxide
b. Feed: 30% PP, 10% oxygen, 11% hydrogen, balance helium, total flow 150 cc/min, atmospheric pressure.

It is seen that the catalyst of Example 8 containing gold and magnesium on a support prepared from titanium isopropoxide achieved an excellent selectivity to propylene oxide, high conversion of propylene, and excellent hydrogen efficiency.

EXAMPLE 9

Titanium isopropoxide (9.40 g) was dissolved in isopropanol (105 g) in a glovebox. The solution was placed into an addition funnel. A flask containing silica (50.0 g of 40/60 mesh Cabot Cab-O-Sil-EH5 fumed silica) was attached to a rotary evaporator. The silica had previously been wetted and dried at 110° C. and calcined at 500° C. The flask containing the silica was cooled to 0° C. with an ice bath. The titanium solution was added to the silica in vacuo at 0° C. Solvent and volatiles were removed at 0° C. in vacuo. The residue was heated to room temperature in vacuo and rotated at room temperature for 30 min. The residue was heated to 50° C. in vacuo and rotated at 50° C. for 30 min, then heated to 80° C. in vacuo and rotated at 80° C. for 30 min. Finally, the residue was heated to 100 aC in vacuo and rotated at 100° C. for 30 min yielding a support of this invention.

A gold solution was made by dissolving chloroauric acid (1.0543 g) into water (2000 cc) and heating to 70° C. The pH was adjusted to 7.5 with sodium carbonate. The support (20.00 g) was added quickly and stirred vigorously at 70° C. The pH was readjusted to 7.5 with sodium carbonate. Magnesium nitrate (2.5010 g) was added to the solution and the pH adjusted with sodium carbonate. The mixture was stirred at 70° C. for 1 hr while keeping the pH at 7.5. Then mixture was cooled to room temperature and the solids were filtered. The solids were added to water (800 cc) of pH 7.5 (from Na₂CO₃) and stirred for 5 min, then filtered. The solids were dried at room temperature for 1 hr by pulling air through the solids on the filter frit. The material was calcined in air from room temperature to 100° C. in 1 hr, then held at 100° C. for 1 hr, then heated in 8 hr to 400° C. and held at 400° C. for 4 hr. The solid (4 g) was heated in air to 500° C., 600° C., and 700° C. and held at each of these temperatures for 4 hr yielding a catalyst of this invention.

Composition by NAA: 41.7 percent Si, 2.96 percent Ti, 0.39 percent Au, 0.21 percent Na, 0.74 percent Mg. Raman spectra of five samples of this catalyst showed no evidence of crystalline titanium dioxide; one sample showed a trace of anatase. UV-VIS DRS (fresh catalyst) exhibited a peak at 291.4 nm. Ti K-edge XANES showed a single peak at +4.30 eV.

The catalyst (2.03 g, 7.0 cc) was tested in the oxidation of propylene with oxygen with the results shown in Table 7. The used catalyst was regenerated a first time as follows. The catalyst was flushed with a mixture of oxygen (10 mole percent) in helium until no propylene was seen on a mass spectrometer. The catalyst was then heated from 140° C. to 350° C. in 1 hr in the oxygen/helium mixture at a flow of 150 cc/min, then held at 350° C. for 1 hr. The catalyst was cooled to 120° C. in the gas mixture and retested in the oxidation process with the results shown in Table 7. The catalyst was regenerated a second time as follows. The catalyst was flushed with a mixture of oxygen (10 mole percent) in helium until no propylene was seen on a mass spectrometer. The catalyst was heated from 120° C. to 350° C. in 1 hr under the oxygen/helium mixture at 150 cc/min and held at 350° C. for 3 hr. The catalyst was cooled to 140° C. in the oxygen/helium mixture and retested in the oxidation process with the results shown in Table 7.

TABLE 7

% PO Sel / % PP Conv (H₂O/PO)$^{a,b}$

| Time (hr) | T (°C.) | % PO Sel. | % PP Conv. | H₂O/PO |
|---|---|---|---|---|
| 0.7 | 100 | 97.7 | 0.200 | 4.50 |
| 1.7 | 100 | 97.2 | 0.164 | 4.91 |
| 2.7 | 120 | 95.4 | 0.296 | 4.85 |
| 3.7 | 120 | 95.4 | 0.274 | 4.78 |
| 4.7 | 140 | 86.4 | 0.435 | 10.17 |
| 5.7 | 140 | 85.3 | 0.362 | 6.30 |
| 18.8 | 140 | 80.9 | 0.202 | 9.08 |
| After first regeneration: | | | | |
| 0.7 | 120 | 92.6 | 0.292 | 4.81 |
| 1.7 | 120 | 95.2 | 0.280 | 3.94 |
| 2.7 | 120 | 92.3 | 0.293 | 4.23 |
| 13.2 | 120 | 93.9 | 0.173 | 8.94 |
| After second regeneration: | | | | |
| 0.7 | 140 | 89.7 | 0.544 | 5.03 |
| 1.9 | 140 | 86.2 | 0.361 | 7.05 |
| 3.1 | 140 | 90.0 | 0.294 | 6.47 |
| 16.2 | 140 | 84.1 | 0.233 | 7.79 |
| 17.6 | 150 | 84.0 | 0.281 | 9.96 | a. % PP conv = mole percentage propylene conversion, % PO Sel = mole percentage selectivity to propylene oxide, H₂O/PO = molar ratio of water to propylene oxide
b. Feed: 30% PP, 10% oxygen, 11% hydrogen, balance helium, total flow 150 cc/min, atmospheric pressure.

It is seen that the catalyst of Example 9 calcined up to 700° C. achieved high selectivity to propylene oxide, good propylene conversion, and high hydrogen efficiency.

EXAMPLE 10

Titanium isopropoxide (1.100 g) was dissolved in isopropanol (27.5 g). The titanium solution was added to silica (PQ CS-1040E, 40/60 mesh; 10.05 g; previously calcined at 300° C.). The mixture was shaken and swirled for about 1 hr. The flask containing the mixture was attached to a rotary evaporator and solvent, and volatiles were removed under vacuum at room temperature for 1 hr. The mixture was heated to 50° C. under vacuum and rotated for 30 min, then heated to 100° C. under vacuum and rotated for 1 hr, and then cooled to 30° C. to form a support of this invention.

A gold solution was made by dissolving chloroauric acid (0.1037 g) in water (400 cc) and heating to 70° C. The pH was adjusted to 7.5 with aqueous sodium hydroxide (0.1 N). The support (5.019 g) was added quickly and stirred vigorously at 70° C. The support and solution were stirred at 70° C. for 1 hour, then cooled to room temperature. All succeeding filtrations and washes were conducted at room temperature. The solids were filtered, then added to water (3000 cc) and stirred for 5 min. The solids were filtered and added to water (3000 cc) three more times. Thereafter, the solids were filtered and dried at room temperature for 30 min and then heated to 100° C. The solids were calcined in air at 100° C. for 12 hr; then heated in 8 hr to 400° C. and held at 400° C. for 4 hr.

Composition by NAA: 41.1 percent Si, 1.61 percent Ti, 0.53 percent Au, 0.11 percent Na. Raman and HR-TEM showed no evidence of crystalline titanium dioxide. UV-VIS exhibited a peak at 304.1 nm.

The catalyst (5.0 cc) was tested in the oxidation of propylene by oxygen with the results shown in Table 8. After 7 hr on stream, the catalyst was regenerated for 2 hr at 350° C. in a mixture of oxygen (15 mole percent) in helium, and retested in the oxidation process with the results shown in Table 8.

TABLE 8

| T (°C.) | Time (hr) | % PP Conv/% PO Sel (H$_2$O/PO) |
|---|---|---|
| 100 | 0.5 | 0.26/64.8 (24.66) |
| 120 | 1 | 0.31/47.1 (55.91) |
| 120 | 2 | 0.22/47.1 (65.02) |
| 130 | 7 | 0.21/36.4 (99.90) |
| After regeneration: | | |
| 120 | 0.5 | 0.37/55.7 (46.4) | a. % PP Conv = mole percentage propylene conversion, % PO Sel = mole percentage selectivity to propylene oxide, H$_2$O/PO = molar ratio of water to propylene oxide.
b. Feed: 30% PP, 10% oxygen, 12% hydrogen, balance helium; total flow rate 150 cc/min, atmospheric pressure.

It is seen that the catalyst of Example 10 produces propylene oxide.

We claim:

1. A process of preparing an olefin oxide comprising contacting an olefin having at least three carbon atoms with oxygen in the presence of hydrogen and an optional diluent, and in the presence of a catalyst comprising gold on a support, wherein the support comprises titanium dispersed on silica, the titanium being present substantially in a disorganized phase.

2. The process of claim 1 wherein the olefin is a C$_{3-12}$ olefin.

3. The process of claim 2 wherein the olefin is propylene.

4. The process of claim 1 wherein the olefin is selected from butadiene, cyclopentadiene, dicyclopentadiene, styrene, α-methylstyrene, divinylbenzene, allyl chloride, allyl alcohol, diallyl ether, allyl ethyl ether, allyl butyrate, allyl acetate, allyl benzene, allyl phenyl ether, allyl propyl ether, and allyl anisole.

5. The process of claim 1 wherein the olefin is used in a quantity greater than 1 and less than 99 mole percent, based on the total moles of olefin, oxygen, hydrogen, and optional diluent.

6. The process of claim 1 wherein the oxygen is used in a quantity greater than 0.01 and less than 30 mole percent, based on the total moles of olefin, oxygen, hydrogen, and optional diluent.

7. The process of claim 1 wherein the hydrogen is used in a quantity greater than 0.01 and less than 50 mole percent, based on the total moles of olefin, oxygen, hydrogen, and optional diluent.

8. The process of claim 1 wherein a diluent is employed.

9. The process of claim 8 wherein when the process is conducted in a vapor phase, the diluent is selected from the group consisting of helium, nitrogen, argon, methane, carbon dioxide, steam, and mixtures thereof; and wherein when the process is conducted in a liquid phase, the diluent is selected from chlorinated benzenes, C$_{1-10}$ aliphatic alcohols, chlorinated C$_{1-10}$ alkanols, and liquid polyethers, polyalcohols, and polyesters.

10. The process of claim 1 wherein the diluent is used in a quantity greater than 0 and less than 90 mole percent, based on the total moles of olefin, oxygen, hydrogen, and optional diluent.

11. The process of claim 1 wherein the gold has an average particle size of 10 Å or greater.

12. The process of claim 11 wherein the average gold particle size is greater than 10 Å and less than 500 Å.

13. The process of claim 1 wherein the gold is loaded onto the support in an amount greater than 0.01 and less than 20 weight percent.

14. The process of claim 1 wherein the titanium loading is greater than about 0.02 weight percent and less than about 20 weight percent, based on the weight of the silica.

15. The process of claim 1 wherein the surface area of the silica is greater than about 15 m$^2$/g.

16. The process of claim 1 wherein the surface area of the silica is greater than about 20 m$^2$/g and less than about 800 m$^2$/g.

17. The process of claim 1 wherein the silica is selected from the group consisting of fumed silicas, silica gels, precipitated silicas, precipitated silica gels, silicalite and mixtures thereof.

18. The process of claim 1 wherein the support is substantially free of crystalline titanium dioxide as identified by high resolution transmission electron microscopy (HR-TEM).

19. The process of claim 18 wherein an HR-TEM image of the support shows essentially no lattice planes separated by about 3.5 Å or about 3.25 Å.

20. The process of claim 1 wherein the support is substantially free of crystalline titanium dioxide as identified by Raman spectroscopy.

21. The process of claim 20 wherein the Raman spectrum of the support exhibits essentially no peaks at about 147 cm$^{-1}$, 155 cm$^{-1}$, 448 cm$^{-1}$, and 612 cm$^{-1}$.

22. The process of claim 1 wherein the disorganized phase is identified by ultraviolet-visible diffuse reflectance spectroscopy (UV-VIS DRS).

23. The process of claim 22 wherein the UV-VIS DRS spectrum of the fresh catalyst exhibits a band at 310 nm or lower wavelengths.

24. The process of claim 20 wherein the disorganized phase is identified by titanium K-edge X-ray absorption near edge structure (Ti K-edge XANES) spectroscopy.

25. The process of claim 24 wherein the support exhibits substantially a single peak at +4.6 eV±1.2 eV in the Ti K-edge XANES spectrum measured relative to an internal metallic titanium standard wherein zero energy is set at 4,966.0 eV.

26. The process of claim 1 wherein greater than 90 weight percent of the titanium in the support is in the disorganized phase.

27. The process of claim 1 wherein greater than 95 weight percent of the titanium in the support is in the disorganized phase.

28. The process of claim 1 wherein the catalyst is bound to a second support.

29. The process of claim 28 wherein the second support is selected from silicas, aluminosilicates, titania, magnesia, carbon and mixtures thereof.

30. The process of claim 1 wherein the process is conducted at a temperature greater than 20° C. and less than 250° C.

31. The process of claim 1 wherein the process is conducted in a gaseous phase at a gas hourly space velocity of the olefin greater than 10 hr$^{-1}$ and less than 50,000 hr$^{-1}$.

32. The process of claim 1 wherein the process is conducted in a liquid phase at a weight hourly space velocity of the olefin greater than 0.01 hr$^{-1}$ and less than 100 hr$^{-1}$.

33. The process of claim 1 wherein the process is conducted in a reactor selected from batch, fixed bed, transport bed, moving bed, fluidized bed, trickle bed, shell and tube, continuous flow, intermittent flow, and swing reactors.

34. The process of claim 1 wherein the process exhibits an olefin conversion of greater than 0.05 mole percent and a selectivity to olefin oxide of greater than 70 mole percent.

35. The process of claim 1 wherein the process exhibits an olefin conversion of greater than 0.5 mole percent and a selectivity to olefin oxide of greater than 90 mole percent.

36. The process of claim 1 wherein the catalyst is active for at least 20 hours.

37. A process of preparing propylene oxide comprising contacting in a gas phase propylene with oxygen in the presence of hydrogen and an optional diluent and in the presence of a catalyst containing gold having an average particle size between 12 Å and 200 Å on a support, the support comprising titanium dispersed on silica, the titanium being substantially in a disorganized phase and substantially free of crystalline titanium dioxide as determined by high resolution electron transmission microscopy, Raman spectroscopy, and/or ultraviolet-visible diffuse reflectance spectroscopy, the contacting being conducted at a temperature greater than 70° C. and less than 225° C.

38. The process of claim 37 wherein the quantity of propylene is greater than 20 and less than 70 mole percent, based on the total moles of propylene, oxygen, hydrogen, and optional diluent.

39. The process of claim 37 wherein the quantity of oxygen is greater than 5 and less than 20 mole percent, based on the total moles of propylene, oxygen, hydrogen, and optional diluent.

40. The process of claim 37 wherein the quantity of hydrogen is greater than 3 and less than 20 mole percent, based on the total moles of propylene, oxygen, hydrogen, and optional diluent.

41. The process of claim 37 wherein the quantity of diluent is greater than 15 and less than 70 mole percent, based on the total moles of propylene, oxygen, hydrogen, and optional diluent.

42. The process of claim 37 wherein the process achieves a selectivity to propylene oxide of greater than 90 mole percent.

43. The process of claim 37 wherein the process achieves a propylene conversion of greater than 0.2 mole percent.

44. The process of claim 37 wherein the productivity to propylene oxide is greater than 0.9 millimoles of propylene oxide per gram catalyst per hour.

45. A composition comprising gold on a support, wherein the composition excludes palladium, the support comprising titanium dispersed on silica wherein the titanium is substantially in a disorganized phase.

46. The composition of claim 45 wherein the gold is present as particles having an average size of 10 Å or greater.

47. The composition of claim 45 wherein the gold is present as particles having an average size of greater than 10 Å and less than 500 Å.

48. The composition of claim 45 wherein the gold is present in an amount greater than about 0.01 and less than about 20 weight percent.

49. The composition of claim 45 wherein the titanium loading is greater than about 0.02 weight percent and less than about 20 weight percent, based on the weight of the silica.

50. The composition of claim 45 wherein the support is substantially free of crystalline titanium dioxide as identified by high resolution transmission electron microscopy (HR-TEM).

51. The composition of claim 50 wherein the HR-TEM image of the support shows essentially no lattice planes separated by about 3.5 Å or about 3.25 Å.

52. The composition of claim 45 wherein the support is substantially free of crystalline titanium dioxide as identified by Raman spectroscopy.

53. The composition of claim 52 wherein the Raman spectrum of the support exhibits essentially no peaks at about 147 $cm^{-1}$, 155 $cm^{-1}$, 448 $cm^{-1}$, and 612 $cm^{-1}$.

54. The composition of claim 45 wherein the disorganized phase is identified by ultraviolet-visible diffuse reflectance spectroscopy (UV-VIS DRS).

55. The composition of claim 54 wherein the UV-VIS DRS spectrum of the fresh catalyst exhibits a band at 310 nm or lower wavelengths.

56. The composition of claim 50 wherein the disorganized phase is identified by Ti K-edge X-ray absorption near edge structure (Ti K-edge XANES) spectroscopy.

57. The composition of claim 56 wherein the support or catalyst exhibits substantially a single peak at +4.6±1.2 eV in the Ti K-edge XANES spectrum measured relative to an internal metallic titanium standard wherein zero energy is set at 4,966.0 eV.

58. The composition of claim 45 wherein greater than 90 weight percent of the titanium in the support is in the disorganized phase.

59. The composition of claim 45 wherein greater than 95 weight percent of the titanium in the support is in the disorganized phase.

60. The composition of claim 45 wherein the surface area of the silica is greater than 15 $m^2/g$ and less than 800 $m^2/g$.

61. The composition of claim 60 wherein the silica is selected from the group consisting of fumed silicas, silica gels, precipitated silicas, precipitated silica gels, silicalite, and mixtures thereof.

62. The composition of claim 45 wherein the composition is extruded with, bound to, or supported on a second support.

63. The composition of claim 62 wherein the second support is selected from silicas, aluminas, aluminosilicates, magnesia, titania, carbon, and mixtures thereof.

64. The composition of claim 45 being prepared by a process comprising contacting the support with a solution containing a gold compound, wherein the pH of the solution is between 5 and 11, at a temperature between 20° C. and 80° C.; and thereafter recovering solids, and optionally washing the solids, and then calcining the solids under air or under a reducing atmosphere or heating the solids in an inert atmosphere at a temperature between 250° C. and 800° C.

65. The composition of claim 64 wherein the soluble gold compound is selected from chloroauric acid, sodium chloroaurate, potassium chloroaurate, gold cyanide, potassium gold cyanide, and diethylamine auric acid trichloride.

66. The composition of claim 64 wherein the pH is adjusted with a base.

67. The composition of claim 66 wherein the base is selected from sodium hydroxide, sodium carbonate, potassium carbonate, cesium hydroxide, and cesium carbonate.

68. The composition of claim 64 wherein the reducing atmosphere is hydrogen.

69. The composition of claim 45 wherein the support is prepared by contacting a silica having reactive hydroxyl groups with a titanium compound which is capable of reacting with the hydroxyl groups under reaction conditions, and thereafter drying the resulting support at a temperature between 0° C. and 150° C. in a vacuum or in a stream of air or in an inert gas.

70. The composition of claim 69 wherein the titanium compound is selected from titanium alkoxides, titanium sulfate, titanium carboxylates, titanium oxysulfate, titanium halides, and organotitanium halides.

71. The composition of claim 69 wherein the titanium compound is selected from titanium isopropoxide, titanium propoxide, titanium ethoxide, and titanium butoxide.

72. The composition of claim 69 wherein the titanium compound is titanium chloride.

73. The composition of claim 69 wherein the contacting is conducted at a temperature between 0° C. and 50° C.

74. The composition of claim 69 wherein after drying the support is calcined in air or in an inert gas at a temperature between 100° C. and 800° C.

* * * * *